United States Patent [19]

Meguro et al.

[11] Patent Number: 4,685,880

[45] Date of Patent: Aug. 11, 1987

[54] CUVETTE BELTS AND MANUFACTURE OF SAME

[75] Inventors: Jun-Ichi Meguro, Huntington Beach; Arne L. Solberg; William A. Stark, both of Costa Mesa; Paul K. Hsei, Huntington Beach, all of Calif.

[73] Assignee: American Hospital Supply Corporation, Evanston, Ill.

[21] Appl. No.: 746,233

[22] Filed: Jun. 18, 1985

[51] Int. Cl.$^4$ ............................................. B30B 15/06
[52] U.S. Cl. .................................. 425/416; 264/554; 356/246; 422/66; 422/102; 425/422; 425/DIG. 48
[58] Field of Search ............... 425/416, 411, 406, 290, 425/344, 412, 422, 423, DIG. 48; 422/66, 102; 356/246; 220/4 E; 264/554; 65/231

[56] References Cited

U.S. PATENT DOCUMENTS

| | | | |
|---|---|---|---|
| 2,442,338 | 6/1948 | Borkland | 264/554 |
| 2,666,951 | 1/1954 | Grove et al. | 425/DIG. 48 |
| 3,203,218 | 8/1965 | Bolt et al. | 425/DIG. 48 |
| 3,341,895 | 9/1967 | Shelby | 425/DIG. 48 |
| 3,346,923 | 10/1967 | Brown et al. | 425/DIG. 48 |
| 3,376,607 | 4/1968 | Brown | 425/416 X |
| 3,396,430 | 8/1968 | Westcott | 425/290 X |
| 3,570,067 | 3/1971 | Jones et al. | 425/416 X |
| 3,620,678 | 11/1971 | Guigan et al. | 422/66 |
| 4,085,177 | 4/1978 | Sauer | 264/554 |
| 4,263,256 | 4/1981 | Morle | 422/66 |

FOREIGN PATENT DOCUMENTS 188617 11/1983 Japan ...................... 425/416

Primary Examiner—Richard L. Chiesa
Attorney, Agent, or Firm—Perman & Green

[57] ABSTRACT

A flexible plastic cuvette belt comprises a series of open-topped chambers defining said cuvettes interconnected by webs. The chambers are generally rectangular in cross-section with their side faces having an approximately flat profile across their widths. The belt is used in conjunction with a photometric analysis station of the clinical analyzer which has a pair of spaced parallel plates which engage the cuvette side faces and render or keep them parallel. The forming press for use in the manufacture of such a cuvette belt is also disclosed.

6 Claims, 13 Drawing Figures

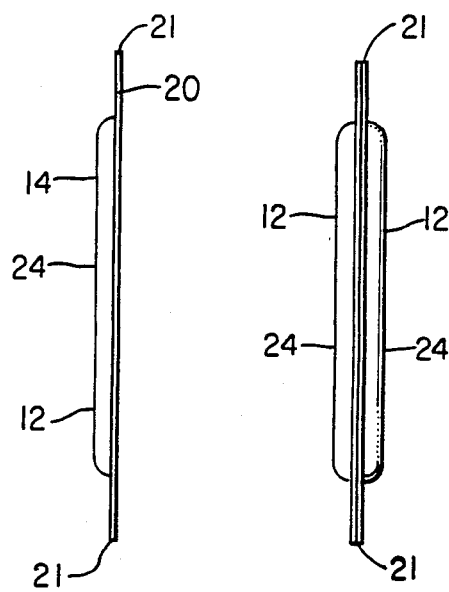
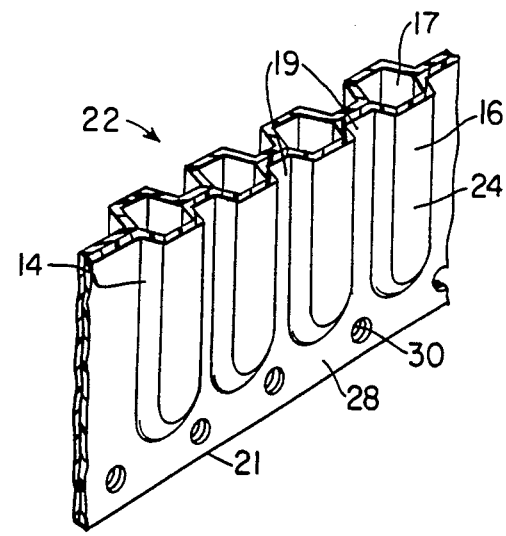
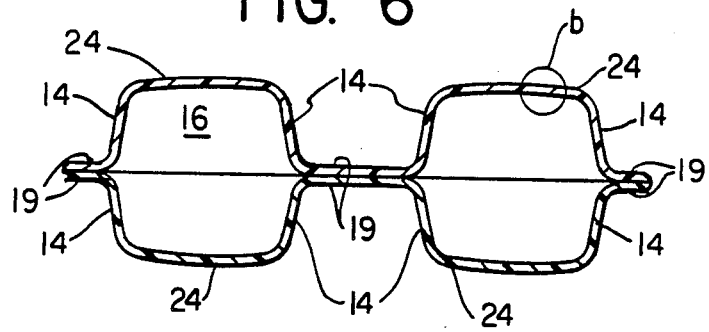
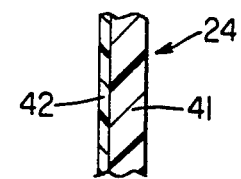
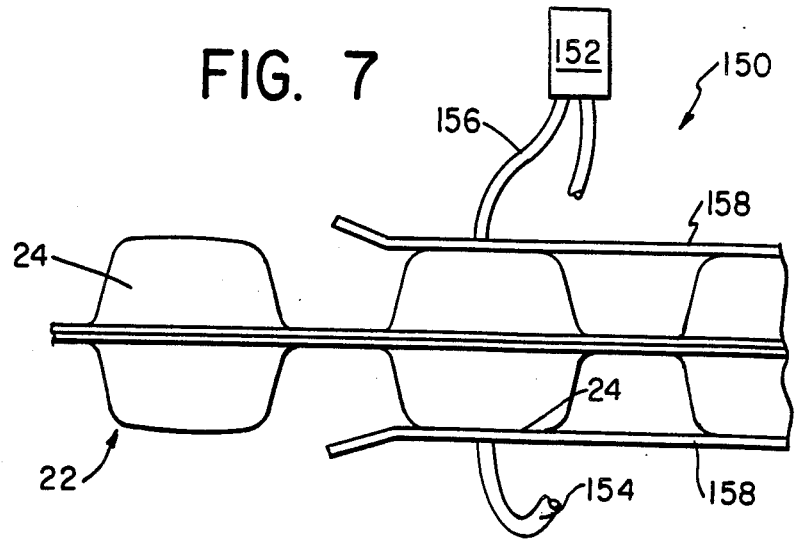

CUVETTE BELTS AND MANUFACTURE OF SAME

INTRODUCTION

The present invention relates generally to cuvettes for use in the chemical analysis of fluid samples in an automated instrument and more particularly to flexible cuvette belts consisting of a plurality of integrally interconnected cuvettes which are designed to be transported through such an instrument, and the manufacture of such belts.

BACKGROUND OF THE INVENTION

A variety of automated or semi-automated chemical analyzers are known which utilize cuvettes for the chemical testing of samples placed therein. Generally, a predetermined amount of liquid sample, such as a biological fluid, is placed in the cuvette which is then transported through the instrument. As the cuvette is being transported, the instrument dispenses a quantity of reagent into the sample and monitors the resulting chemical reaction. Such monitoring is generally accomplished through use of an optical means which views the fluid sample through optically transparent portions of the cuvette.

In order to simplify the loading of the cuvettes into the instrument and facilitate their handling by the instrument once so loaded, proposals have been made to provide the cuvettes in the form a continuous integral strip. The individual cuvettes of the strip are designed to be relatively rigid, but the strip itself is provided with sufficient flexibility to ease its transport through the instrument. Furthermore, by making the cuvettes in a continuous strip form, they can be manufactured relatively inexpensively from suitable plastic material, thereby permitting their disposal after use. This is an important feature since it avoids the requirement for washing the cuvettes after use and avoids any possibility of cross contamination of fluid samples which could cause erroneous test results. A proposed cuvette system designed to meet these requirement is disclosed in U.S. Pat. No. 4,263,256.

In commonly owned copending U.S. patent application Ser. No. 559,016 and entitled "Cuvette Ssytem For Automated Chemical Analyzer", which is a continuation of U.S. patent application Ser. No. 284,842 filed July 20, 1981, both now abandoned, the disclosure of which applications are hereby incorporated by reference in their entirety herein, there is described a cuvette belt which comprises a matching pair of elongated, formed plastic strips which are joined together along corresponding faces thereof to form an integral belt. A series of regularly spaced chamber halves are formed transversely in each of the corresponding strip faces which define open-topped cuvette receptacles when the belt halves are joined.

As described, the cuvette belt is made by forming strip plastic material with a series of regularly spaced transverse (laterally extending) formed pockets so as to define two integral side-by-side belt halves. The formed strip is then divided longitudinally to separate the belt halves and the belt halves brought into register and joined together to form a completed cuvette belt.

Using such manufacturing techniques, cuvettes may be obtained with superior operating characteristics and dimensional accuracy previously obtainable only through use of injection molding techniques. This is important when optically analyzing samples in the cuvettes for which a precisely defined optical path through the cuvettes is required.

It is pointed out that it is possible-by utilizing cold forming techniques to avoid optical degradation of the material due to heat. Further, an optical portion of the material may be restrained by clamping or other forming techniques during the pocket forming operation to avoid stretching or other deformation of portions of the pocket which form the sides of the cuvette. In this manner essentially all stretching of the material during the forming is limited to the side walls of the pockets and optical portions thereof are maintained stress-free and with a uniform thickness. Further, as described in the aforesaid application, the opposite side walls of each cuvette chamber, which form the optical portions, are made parallel thereby providing an optical path of precise length through the cuvette.

Reference is also made to commonly owned copending U.S. patent application Ser. No. 746,231, filed June 18, 1985, entitled "Cuvette Belt Manufacture and Process", the disclosure of which application is hereby incorporated by reference in its entirety herein. In that application is disclosed an alternative method for making cuvette belts of the kind comprising a matching pair of plastic strips, each of which is formed with chamber halves and which are joined together to form an integral cuvette belt with the chamber halves aligned to form the cuvette.

According to that method, the two strips of plastic material are identically formed with a series of regularly spaced formed pockets so as to define two integral side-by-side belt halves. The two formed strips are brought into register and joined together to form a composite strip defining two integral mirror image cuvette belts joined by their cuvette mouth ends. The composite strip is then divided longitudinally to separate the cuvette belts.

The present invention is concerned with improved techniques for the manufacture of such cuvette belts with·the particular aim of controlling the optical characteristics of the cuvettes. Accordingly it is an object of the invention to provide a cuvette belt in which the optical path through the cuvettes is precisely defined and repeatable from one cuvette to the next when utilizing the belt in a chemical analyzer.

SUMMARY OF THE INVENTION

This is achieved essentially by manufacturing the cuvette belt with the cuvette chambers having side walls such that when a cuvette is located at an optical analysis station it can be located between ·transparent plates which serve to flatten and space the cuvette side walls so that they are arranged precisely parallel to each other and the optical path is extremely accurately defined. In this way slight variations in the curvature of the walls do not effect the preciseness of the optical path. This alleviates or obviates one of the problems with the previous cuvettes which is that it is very difficult to insure that the unsupported side walls of the cuvettes are accurately parallel.

The present invention also provides forming apparatus for use in the manufacture of such cuvette belts which includes clamping surfaces for clamping the strip material around the pocket zones and forming punches movable through openings in the clamping surfaces to form the pockets in the strip material clamped between the surfaces. The ends of the die punches are convexly radiused to form the bases of the pockets (which form the sides of the cuvettes) with convex profiles across their widths.

According to a preferred and novel feature of the invention, in order to prevent the plastic material in contact with the ends of the die punches from sliding thereover, the ends of the punches are highly polished. This technique insures that the material in contact with the die punch ends is not deformed or stretched during the forming operation so that the stretching of the material is substantially limited to the side walls of the pockets thus providing the side walls of the cuvettes with optical portions that are maintained stress-free and with a uniform thickness. In addition, the sidewalls and top radius of the punches have a rougher surface than the ends thereof to prevent adherence of the cuvette material to the punches and to prevent undesirable wrinkling of the material especially during the time of punch retraction.

In a preferred embodiment of the forming press according to the invention, a series of die punches is provided along each side for punching indexing holes along each side of the strip material. These punches act prior to the pocket forming die punches and after the clamping surfaces have come together.

It will be understood that the press operates on the strip material in batch mode and the strip material is indexed therethrough. The indexing means should accurately and precisely control the advance of the strip to insure that all the pockets and indexing holes are equally and regularly spaced along the entire strip.

Also subject to this invention is the combination of the cuvette belt as described above and a photoanalysis apparatus including transparent plates between which the cuvette belt is passed to flatten the side walls of the cuvettes into parallel relation.

DESCRIPTION OF THE DRAWINGS

Other features and advantages of the present invention will become apparent from the following description taken in conjunction with the accompanying drawings wherein:

FIG. 3 is an end view of the formed strip shown in FIG. 2, FIG. 4 is an end view of a composite strip formed by joining together two formed strips as shown in FIG. 2, FIG. 5 is a perspective view of a cuvette belt produced by dividing longitudinally along its centerline, the composite strip of FIG. 4, FIG. 6 is a horizontal cross-section through the cuvette belt shown in FIG. 5, FIG. 6a shows a wall section b of the cuvette, FIG. 7 shows the manner of acting upon a cuvette belt according to the invention when taking readings at a photoanalysis station of the chemical analyzer.

DESCRIPTION OF THE PREFERRED EMBODIMENTS

Figure 1:
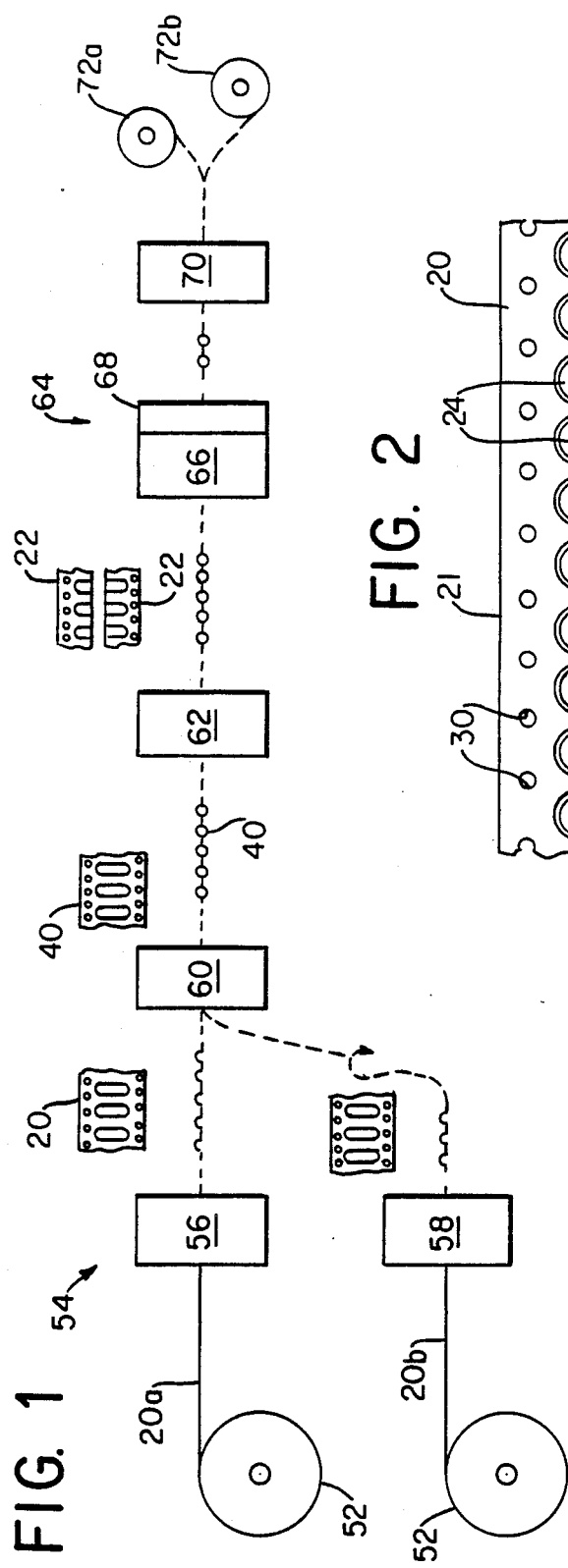
FIG. 1 is diagrammatic side elevation of an embodiment of automatic equipment for making cuvette belts from strip plastic material incorporating forming apparatus according to this invention.

Referring to the drawings, FIG. 1 illustrates diagrammatically an embodiment of automatic systems for producing plastic cuvette belts as shown in FIGS. 5 and 6 which includes forming apparatus according to the present invention. Such automatic cuvette making system is described in detail in our aforesaid copending U.S. patent application Ser. No. 746,231 entitled "Cuvette Belt Manufacturing Apparatus and Process". However, such system is only described in outline herein to the extent necessary for an understanding of the subject of the present invention and for a detailed understanding of that system reference should be had to the aforesaid copending application.

Referring now to FIG. 1, there is shown one embodiment of apparatus for making cuvette belts from strip plastic material which is advanced in turn to an in-line series of processing stations to produce the completed belts. The apparatus illustrated simultaneously forms two cuvette belts 22 from two strips of plastic material 20.

Figure 2:
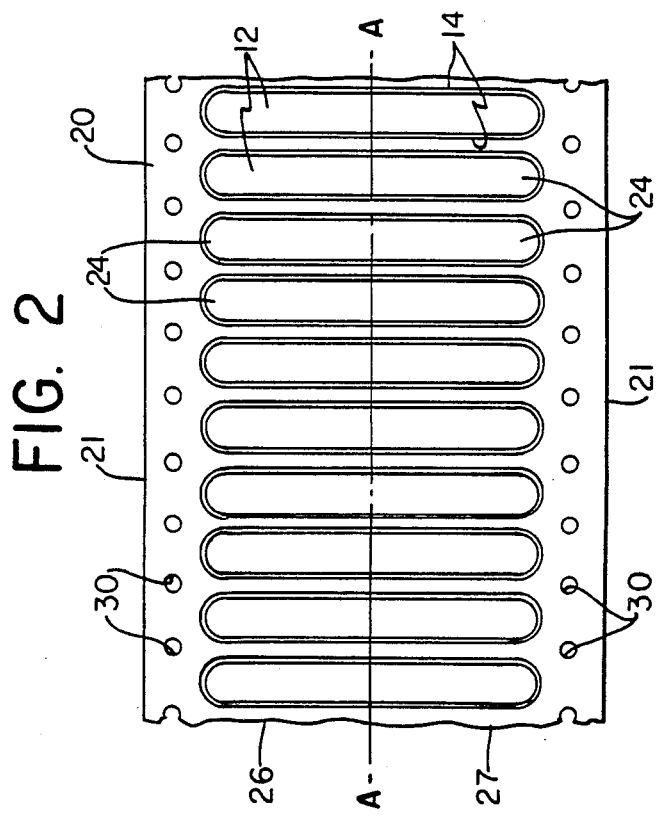
FIG. 2 is a top plan view of a strip of plastic material following formation thereof in a forming press of this invention.

Each strip 20 is fed from a reel 52 and is formed at the forming station 54 in a respective forming press 56, 58 with regularly spaced, transverse pockets 12 so as to define two integral side-by-side mirror image belt halves (FIGS. 2 and 3).

The two formed strips are then brought into face-to-face register and joined together at a sealing station 60 to form two integral side-by-side mirror image cuvette belts (FIG. 4). The joined strips are thereafter slit longitudinally along their center lines at a slitting station 62 to produce two identical cuvette belts 22 in a single operation (one of which is shown in FIGS. 5 and 6).

The cuvette belts 22 are formed from preformed strips of plastic material which are suitably obtained by slitting sheet stock material into strips. These strips should be of sufficient length to provide completed cuvette belts of the desired length and in particular of sufficient length to permit the continuous operation of an automated clinical analyzer in which they are to be used. For example, the desired length of the cuvette belt for use in a Paramax Analytical System as manufactured by American Hospital Supply Corporation is 2,000 cuvettes long.

An important feature of the cuvette belt for use in such an analyzer is that the individual cuvettes have closely controlled dimensional accuracy and provide a precisely defined optical path through the cuvette. It has been found that copolyester or vinyl plastic strip stock in thickness of about 0.005 to 0.010 inch provides satisfactory results when formed according to the present invention. A suitable example of such material is KODAR brand Thermoplastic Copolyester Resin manufactured by Eastman Chemical Co., of Rochester, N.Y.

In order to facilitate the fabrication and assembly of the cuvette belt, the strip stock is preferably a laminate having a layer of easily sealable and biologically insert material such as SURLYN brand Ionomer Resin Material manufactured by E.I duPont de Nemours and Co., Inc. of Wilmington, Del. As shown in FIG. 6a, the SURLYN 41 is provided on the inside of the KODAR 42 in the finished cuvette.

In the manufacture of cuvette belts 22 using the apparatus and process of this invention, two strips 20 of stock plastic material as described above are identically formed with regularly spaced formed transverse pockets 12 as shown in FIGS. 2 and 3. Each formed strip defines two integral side-by-side mirror image belt halves 26, 27.

The pockets are formed as narrow shallow indentations having a generally rectangular shape utilizing cold forming techniques to avoid any optical degradation of the strip material due to heat. An optical portion is formed by the base portion 24 of each pocket 12 by restraining the base portion by clamping or other forming techniques during the pocket forming operation to avoid stretching or any other deformation thereof which would be detrimental to its optical performance. In this manner essentially all stretching of the material during forming is limited to the portions forming the sidewalls 14 of the pockets (which eventually form the end walls of the resulting cuvettes; FIG. 5) and the optical portions 24 are maintained stress-free and with a uniform thickness.

During forming, a series of regularly spaced indexing perforations 30 are formed along opposite longitudinal edges of the strip material. These perforations 30 are utilized in the clinical analyzer in which the cuvette belt 22 are to be used precisely to control the transport of the cuvette belts through the analyzer.

The perforations may also be used in the apparatus of FIG. 1 for driving the form strips therethrough for subsequent processing and in particular for accurately aligning the strips when they are brought together in precise registration prior to joining the strips together at the sealing station 60 in the manner explained below.

During transport of a cuvette belt 22 through a clinical analyzer as aforesaid, the cuvettes are aligned with various processing stations including one or more photoanalysis stations. During such photoanalysis it is important that the optical window of the cuvette, i.e. that portion viewed by the analysis instrument, be accurately aligned with the analysis system. For this reason it is important to maintain a precise relationship between the indexing perforations and the optical windows of the cuvette and, accordingly, the edges of the strip may, like the base portions of the pocket, be clamped during the forming process.

In a preferred embodiment, the optical windows are those parts of the optical portions 24 which are located at opposite ends of the pocket 12 in order to insure to the greatest possible extent that the aforesaid precise alignment is repeatedly maintained during transport of the cuvette belt 22 through the analyzer.

After formation of the pocket 12, the two strips 20 are brought together in face to face relationship as shown in FIG. 4 with the pocket 12 and the perforations 30 in precise registration and so that the pairs of opposing pockets 12 together form closed chambers 18. The registered strips are then heat sealed together to form a composite strip 40 defining two integral side by side mirror image cuvette belts joined together by their mouths or open ends.

If the two strips 20 are formed in mirror-image relation with their open pocket 12 facing each other, they can straight forwardly be brought together in the appropriate face to face relation. However it is preferred to form the strips one above the other or adjacent one another with their open faces both facing downwardly, in which event the lower strip 20b must be twisted through 180° about its longitudinal axis (as shown in FIG. 1) prior to bringing the strips 20 together.

It has been found that the formed strips 20 may be joined together by a heat sealing process maintained at a relatively low temperature if a laminate material such as SURLYN is utilized, or by impulse bonding techniques if higher melting point materials are utilized. This is because SURLYN is sealable at a lower temperature than KODAR. It is also possible to utilize other joining methods such as adhesive bonding so long as the optical characteristics and dimensional tolerances of the cuvettes are not adversely affected thereby.

Following the heat sealing step, the composite strip 40 is advanced to the slitter 62 where it is divided longitudinally down its centerline to separate the two cuvette belts 22. The two completed cuvette belts 22 are each as shown in FIGS. 5 and 6 and comprise a series of open-topped chambers 17 separated by thin webs 19 and having a web-like transport area 28 along its lower edge having the indexing perforations 30 formed therein. As seen particularly in FIG. 6, the cuvettes are generally rectangular in cross section and the sidewalls of the cuvettes are approximately flat. In accordance with an alternative embodiment of the present invention, the sidewalls of the cuvettes can be deliberately given a convex or outwardly curved profile.

Following slitting, the completed cuvette belts are advanced to an inspection station 64 where they are checked for defects. Associated with the inspection station is a leak detector 66 and a marking device 68 for applying a machine readable mark to faulty cuvettes in response to detection thereof. This mark is read at the cutting station 70 arranged following the inspection station 64 to cause the cuvette belt to be cut ahead of and behind the faulty cuvette to remove it from the cuvette belt before it is wound on a storage spool. Preferrably, the cutting station includes a counter which counts a predetermined number of cuvettes following a faulty cuvette before effecting the second cut to avoid unnecessary operation of the cutter in the event of a faulty length of cuvette belt 22 occurring.

Reference is made above to the importance of the optical characteristics of cuvettes used in analysis equipment employing photoanalysis of samples contained in the cuvettes. It is particularly important that the optical path through the cuvettes be precisely defined and repeatable from one cuvette to the next to avoid variations in analytical readings due to the cuvettes themselves. In order to achieve this, care is taken to insure that, so far as possible, the opposite side walls of the cuvette through which the optical paths pass are substantially parallel when they are formed in the forming press 56, 58.

The photoanalysis station or each such station of the clinical analyzer is provided with a pair of transparent means, e.g., glass plates between which the cuvettes are passed as the belt is advanced through the photoanalyzer. FIG. 7 illustrates a photometric analysis station 150 of the clinical analyzer which is connected to a photo-optical system 152 by light guides 154, 156 in the manner described in detail in commonly owned copending U.S. patent application Ser. No. 848,851, filed on Apr. 4, 1986 which is a continuation of Ser. No. 575,924 filed on Feb. 1, 1984, now abandoned and entitled "Clinical Analysis Systems and Methods", the disclosure of which is hereby incorporated by reference herein in its entirety.

The photometric analysis station 150 includes a pair of spaced apart vertical glass plates 158 between which the cuvettes are disposed at the stations. The spacing of the plates 158 is chosen so as to coact with the cuvettes to keep flat or make flat the side walls or side portions 24 thereof and render them precisely parallel. For instance, in one embodiment, the distance between the plates is approximately 0.020 to 0.030 inches narrower than the width of formed cuvettes. With this arrangement a greater assurance of such parallelism is achieved than with the prior unsupported cuvette walls.

Figure 8:
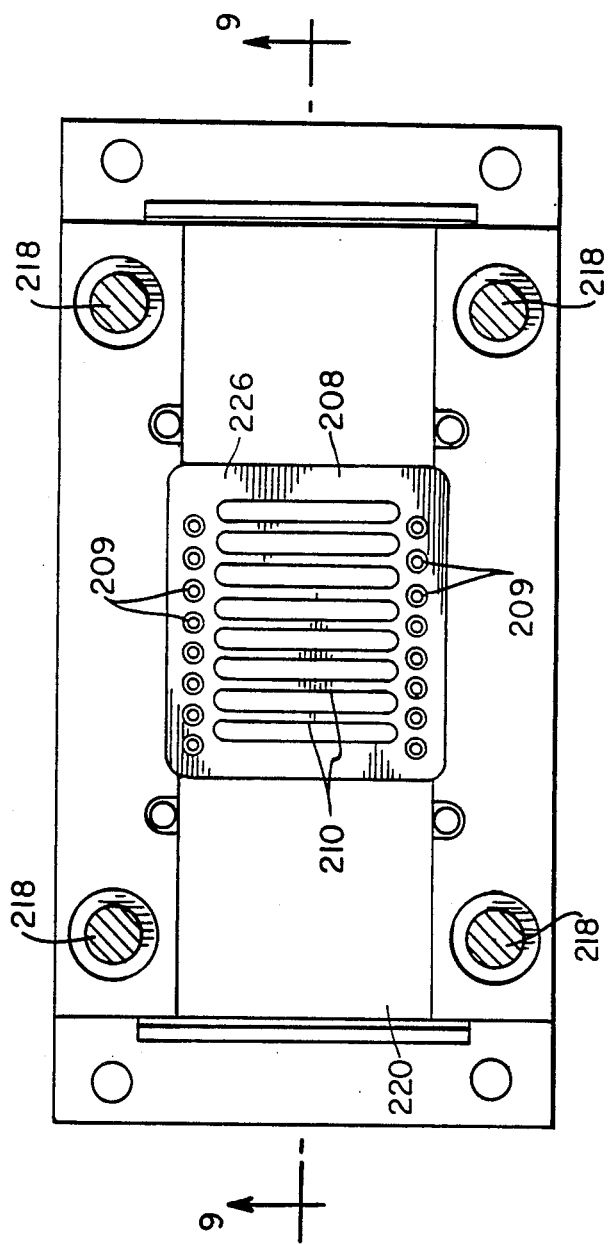
FIG. 8 is a diagrammatic view of an embodiment of the forming press according to the invention taken through line 8—8 of FIG. 9.

An embodiment of forming press according to the invention will now be described in detail with reference to FIGS. 8-11. The press includes a movable upper pressure plate 202 containing an upper die block 204 and a lower pressure plate 206 containing a lower die block 208. The lower die block 208 has a series of opening 210 which as seen in FIG. 8 correspond in shape to the transverse pockets 12 to be formed in the strip 20. Within these openings are respective forming punches 212 mounted for reciprocal movement between retracted positions within the openings 210 and advance positions in which they project, when the die blocks are closed together, into corresponding openings 214 formed in the upper die block.

As also seen in FIG. 8, the lower die block 208 is foemd with two rows of small circular openings 209 along opposite sides, respectively, of the transverse openings 210. Corresponding openings 211 are provided in the upper die block 204 (see FIG. 10). Two series of further die punches 216 mounted on the upper side of the press and movable through the corresponding openings 209, 211 in both die blocks 204, 208 form the indexing perforations 30 in the strip 20.

The upper pressure plate 202 is in two parts 202a and 202b mounted for vertical sliding movement on four leader pins 218 which guide the forming punch assembly in a two stage action as described below. The die punches 216 are fixed to the upper plate part 202a. The forming punches 212 are mounted on a holder 222 and are driven by hydraulic rams 224, the lower position thereof being determined by stops 223.

A table 220 is provided at the entry end of the press for guiding plastic strip to be formed as it enters the press.

In the operation of the forming press, a virgin portion of strip material is advanced into the press and the upper pressure plate 202 actuated to drive the two parts thereof, which are slightly spaced, downwards together. In the closed position of the lower part 202b, the strip 20 is firmly clamped between the opposing surfaces of the die blocks 204, 208. Continued downward movement of the upper pressure plate part 202a advances the die punches 216 through the strip material 20 to cut out the indexing perforations 30.

Now the rams 224 are actuated to drive the pocket forming die punches 212 upwardly from their retracted positions within the openings 210 in the lower die block 208 to form the pockets 12 in the strip 20.

Following this the punches 212 are withdrawn and the upper pressure plate retracted to open the press. The strip 20 is then indexed forward to bring a fresh portion of strip into position for forming. It will be realized that the strip indexing needs to be closely controlled to insure that the spacing between adjacent end pockets of two separately formed sections of strip is exactly as that between adjacent pockets within each section.

Figure 11:
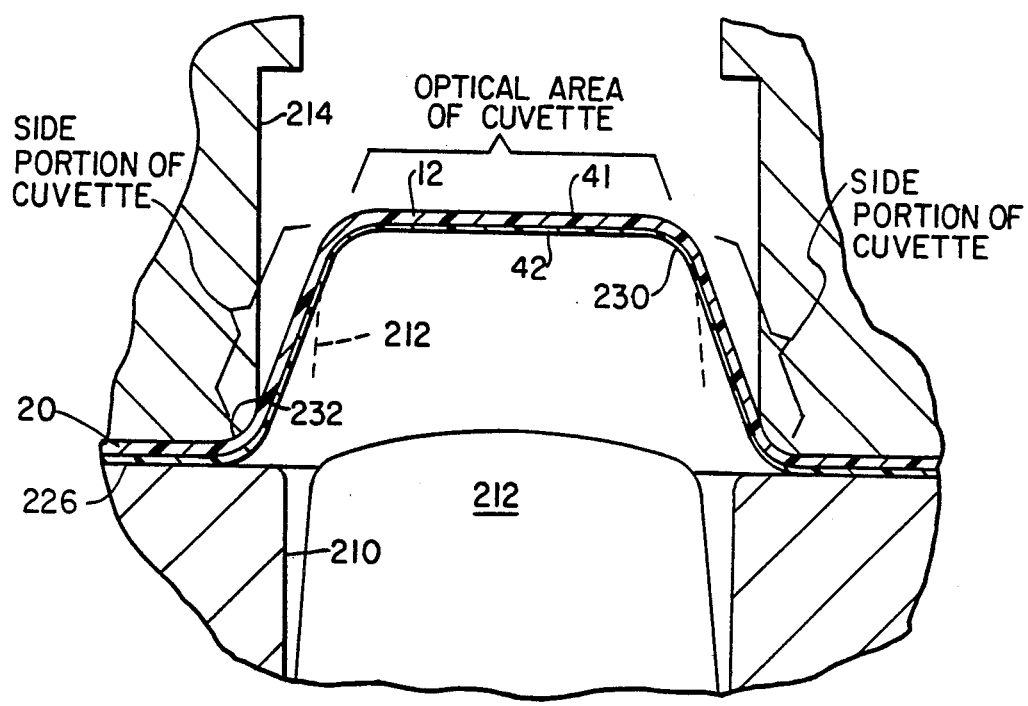
FIG. 11 is a view taken at a in FIG. 9 of the pocket forming punch assembly of the press.

As explained above, the sides of the cuvettes should be substantially flat for the photometer to operate perfectly accurately. Alternatively, the sides of the cuvettes can be made with a convex (outwardly curved) profile across their widths which are flattened at the photometer. The transition between the sidewalls 212b and the ends 212a of the die punches 212 is radius 212c as shown in FIG. 11. The radii of the punch ends are chosen to produce the desired bulging effect in the bases 24 of the pockets (which form the side portion, or stretched portion of the strip, of the cuvette subsequently fabricated therefrom).

Figure 12:
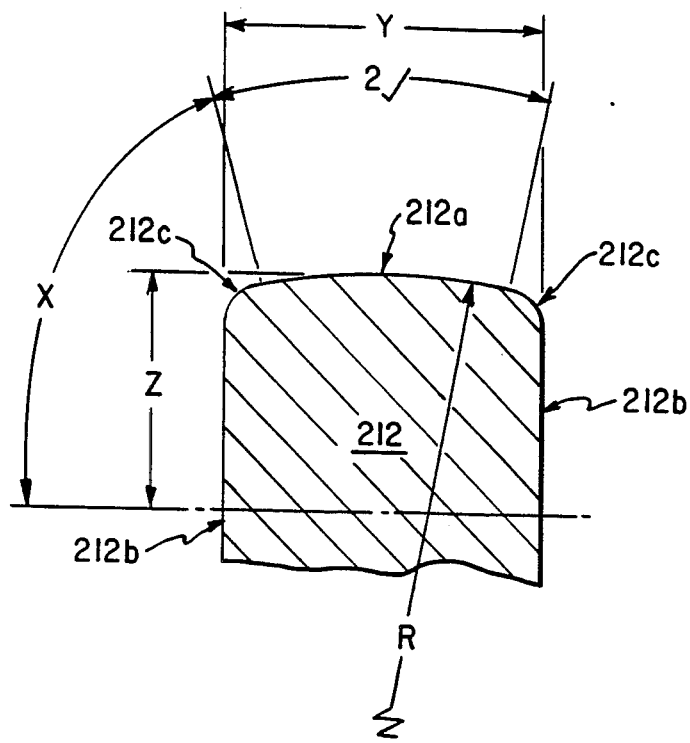
FIG. 12 is a diagrammatic view of the punches 212 showing the detail thereof.

The configuration of punches 212 is seen clearly in FIG. 12 which is an enlarged view of a punch taken from the same side thereof as shown in FIG. 11. End 212a has a high polish thereon, in the order of a 2-6 finish as shown, and preferably 4-6 range finish. The radii 212c and immediate upper portion of sidewalls 212b, shown as "X", have a relatively rougher surface preparation equal to approximately a 32-40 ground finish all around the punch which extends down from the very end of the punch at least about 0.15 inches as shown by "Z". The radii across the end 212a of the punch can be approximately 0.40 inches as shown by "R" for a punch size "Y" of about 0.20 inches. The above dimensions are only a representative of one configuration of the punch and may change depending upon the size of the cuvette pockets to be formed. All surface texture designations are in accordance with ASA B46 standards.

It will be seen that in the retracted position of the die punch 212, it is slightly below clamping surface 226 of the lower die block 208. As the punch is advanced, the strip material is formed therearound. The end surface of the punch is highly polished so that the plastic (SURLYN) material in contact with it does not slide relative to the punch but stays totally registered with it. In this way all the deformation that occurs in forming the pocket occurs in the side walls 14 of the pocket. As a result, that portion of the cuvette wall through which the photometer acts remains the same thickness as the original material and does not deform or stretch in any manner during the forming operation.

As seen in FIG. 11, the stretching takes place in the free, unsupported material between the radiused side edge 230 of the forming punch 212 and the radiused lower edge 232 of the side wall of the opening 211 in the upper die block 204.

There are a number of other aspects of the forming process for the cuvette which are important. A vacuum is created in the openings 214 in the upper die block 204 to aid the forming of the cuvette as the forming punch 212 is activated on the strip material 20. This vacuum has a tendency to suck the material away from the punch 212, although it really does not do so as the punch moves upwards into the opening 211. This vacuum also helps retain the wall of the formed pocket as the punch retracts back into the lower die block 208 and this avoids collapse of the pocket. Also this vacuum pressure strips the formed cuvettes off the bottom half of the die.

Just before the dies open, an air pressure is caused to shoot around the punches 212 towards the inside of the pocket 12 that has just been made in the strip material 20 and separates the material from the forming punches.

This also avoids collapse of the pocket as the punch is retracted.

There is also a positive pressure on the upper die block to help release the formed strip from the upper die block 204. The cuvette pocket should come away from the die pocket before indexing to minimize the chance of any damage to it during indexing. This prevents wrinkling of the pockets 12 during indexing. The vacuum pressure is critical to maintaining the pocket (as the punch is retracted); it is kept at about 20 inches of mercury during forming and when the die is fully open, it is shut off. The positive pressure starts as soon as the vacuum shuts off.

Figure 9:
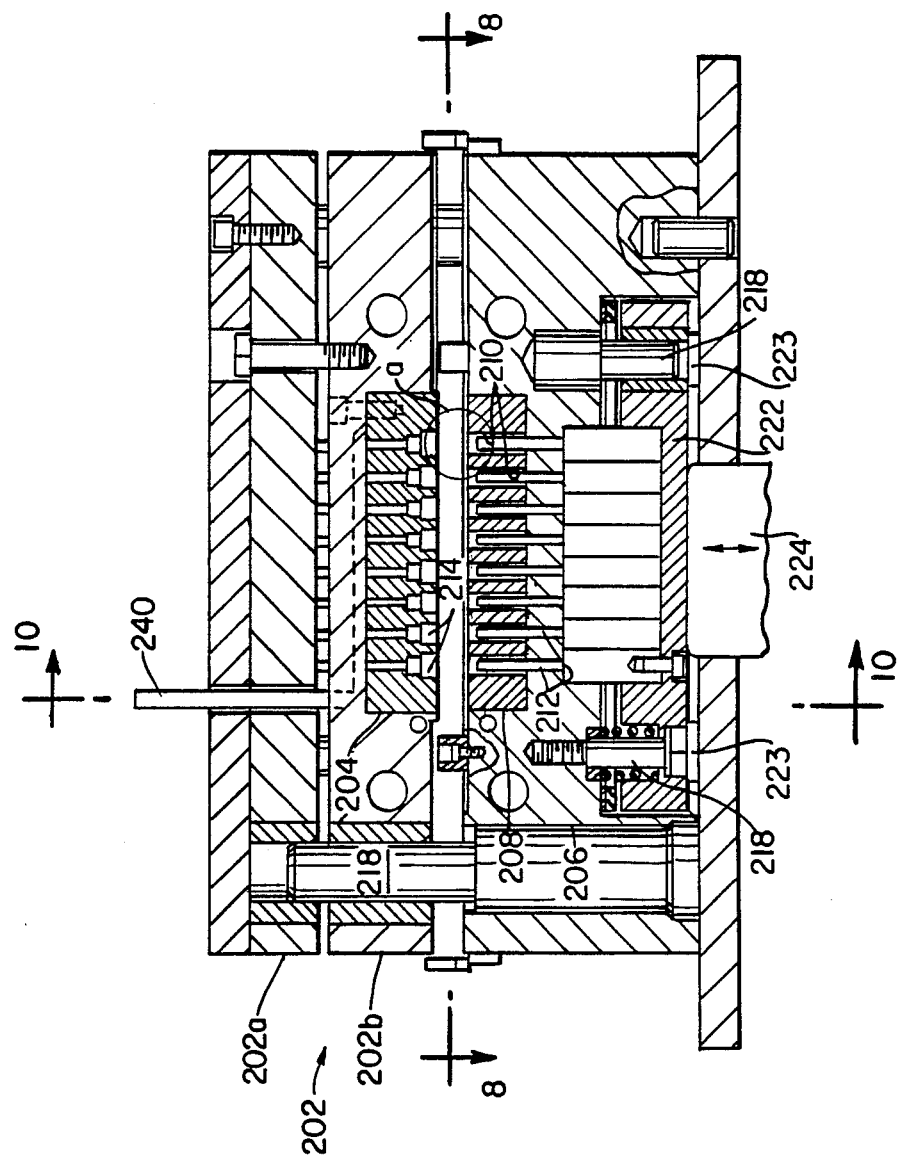
FIG. 9 is a diagrammatic view of a vertical side-section through the forming press of FIG. 8 taken along the line 9—9 of that figure.
Figure 10:
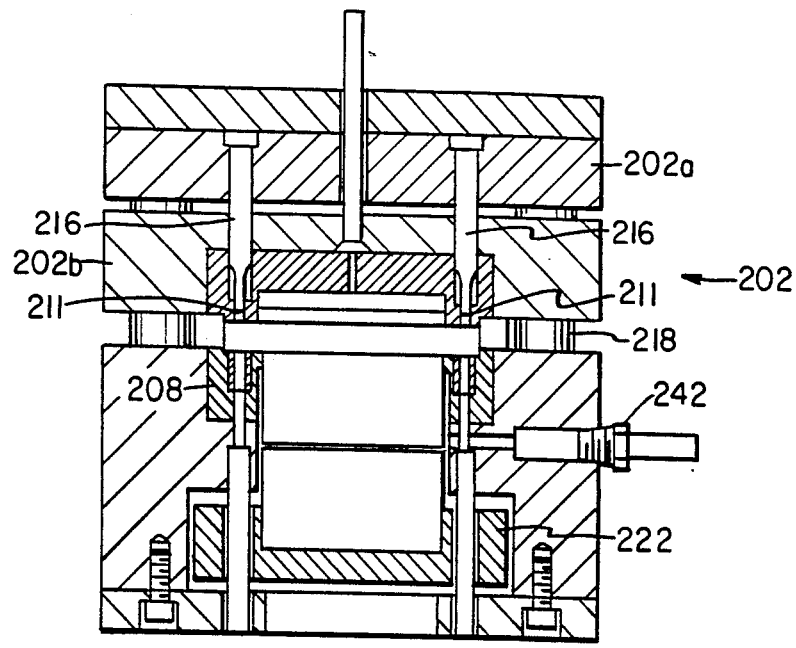
FIG. 10 is a diagrammatic view of a vertical end section through the forming press of FIG. 8 taken along the line 10—10 of FIG. 9.

As shown in FIGS. 9 and 10, the vacuum and positive pressure is applied to openings 214 in the upper die block 204 through a vacuum tube 240 and air under pressure is supplied to openings 210 in the lower die block 208 around the die punches 212 through a supply tube 242.

Although particular configurations and features of the present invention have been discussed with the above described preferred embodiments. thereof, it should be understood that those skilled in the art may make various changes, modifications and substitutions thereto without departing from the spirit and scope of the invention as defined in the appended claims.

We claim:

1. In a forming press apparatus in the manufacture of cuvette belts by cold forming plastic strip material with a series of regularly spaced transverse elongated pockets, said apparatus including:

first and second die members respectively defining first and second clamping surfaces and having openings formed in both said clamping surfaces corresponding to the positions of said pockets, a plurality of forming punches mounted in said openings in said first clamping surface and movable through said openings in said second clamping surface with said punches spaced within said openings in said second clamping surface, means for driving said clamping surfaces together to clamp said strip material therebetween.

means for advancing said forming punches from within said openings in said first clamping surface through said openings in said second clamping surface, after said surfaces have come together, to deform said strip material to form said pockets in the strip material by interaction between the ends of the punches and the edges of the corresponding openings in the second clamping surface, and means for inhibiting stretching of the strip material over the end surfaces of said punches, said punches being spaced within the corresponding openings in the second clamping surface whereby the strip material is in a free, unsupported state between the inner edge of each opening in the second clamping surface and end of the associated forming punch when the latter is advanced through said opening so as to permit stretching of said strip material to form said pockets, the ends of the forming punches being convexly radiused to form the bases of the pockets with approximately flat profiles across their width in the direction along the length of the strip.

2. A forming press apparatus as defined in claim 1 including die punches for punching index holes along each side edge of the strip, said die punches acting prior to operation of said pocket forming punches and after said clamping surfaces have come together.

3. A forming press apparatus as defined in claim 1, in which said means for inhibiting stretching of the strip material over the end surfaces of the punches comprises the end surfaces of the punches being highly polished so that the plastic material in contact with a said end surface does not slide over the end surface.

4. A forming press apparatus as defined in claim 1 including means for creating a vacuum in the openings in said second die member during advancing movement in the pocket forming die punches.

5. A forming press apparatus as defined in claim 4 in which said vacuum is maintained during retraction of the pocket forming die punches.

6. A forming press apparatus as defined in claim 1 including means for introducing air under pressure against the formed strip around said pocket forming die punches before and during retraction of said die punches.

* * * * *